United States Patent
Karami

(10) Patent No.: US 7,172,584 B2
(45) Date of Patent: Feb. 6, 2007

(54) SANITARY ELASTICIZED MALE GUARD

(75) Inventor: Hamzeh Karami, Lockhaven, PA (US)

(73) Assignee: First Quality Products, Inc., State College, PA (US)

( * ) Notice: Subject to any disclaimer, the term of this patent is extended or adjusted under 35 U.S.C. 154(b) by 386 days.

(21) Appl. No.: 10/208,615

(22) Filed: Jul. 30, 2002

(65) Prior Publication Data

US 2004/0024377 A1 Feb. 5, 2004

(51) Int. Cl.
- *A61F 13/471* (2006.01)
- *A61F 13/475* (2006.01)
- *A61F 13/534* (2006.01)

(52) U.S. Cl. .................... 604/385.24; 604/385.03; 604/378

(58) Field of Classification Search ........... 604/385.24, 604/385.23, 385.05, 385.04, 367, 378, 385.14, 604/385.03

See application file for complete search history.

(56) References Cited

U.S. PATENT DOCUMENTS

| | | | | |
|---|---|---|---|---|
| 4,579,556 A | * | 4/1986 | McFarland | 604/385.26 |
| 4,668,230 A | * | 5/1987 | Damico et al. | 604/385.25 |
| 4,770,657 A | * | 9/1988 | Ellis et al. | 604/385.31 |
| 4,865,597 A | * | 9/1989 | Mason et al. | 604/385.31 |
| 5,129,893 A | * | 7/1992 | Thoren | 604/385.25 |
| 5,411,498 A | * | 5/1995 | Fahrenkrug et al. | 604/385.22 |
| 5,542,941 A | * | 8/1996 | Morita | 604/385.04 |
| 5,558,659 A | * | 9/1996 | Sherrod et al. | 604/385.26 |
| 5,558,734 A | * | 9/1996 | Sherrod et al. | 156/164 |
| 5,607,414 A | * | 3/1997 | Richards et al. | 604/378 |
| 5,653,842 A | * | 8/1997 | Kuen | 156/227 |
| 5,855,573 A | * | 1/1999 | Johansson | 604/385.17 |
| 6,315,765 B1 | * | 11/2001 | Datta et al. | 604/385.24 |
| 6,878,138 B2 | * | 4/2005 | Tsuji et al. | 604/385.09 |
| 2001/0009992 A1 | * | 7/2001 | Boulanger et al. | 604/385.04 |
| 2001/0021836 A1 | * | 9/2001 | Kashiwagi | 604/385.24 |
| 2002/0007163 A1 | * | 1/2002 | Boulanger et al. | 604/366 |
| 2002/0007172 A1 | * | 1/2002 | Takei et al. | 604/366 |
| 2003/0088226 A1 | * | 5/2003 | Takagi et al. | 604/385.16 |
| 2003/0171732 A1 | * | 9/2003 | Heyrman et al. | 604/385.27 |
| 2003/0208173 A1 | * | 11/2003 | Lagerstedt-Eidrup et al. | 604/367 |
| 2004/0006323 A1 | * | 1/2004 | Hall et al. | 604/385.24 |

* cited by examiner

*Primary Examiner*—Tatyana Zalukaeva
*Assistant Examiner*—Keshia Gibson
(74) *Attorney, Agent, or Firm*—Amster, Rothstein and Ebenstein LLP

(57) ABSTRACT

A disposable sanitary absorbent article such as an absorbent pad (e.g., male guard) is provided which is defined by opposed lateral sides and opposed longitudinal sides extending between said lateral side, comprising a topsheet, a backsheet and an absorbent core disposed therebetween having opposed lateral sides and opposed longitudinal sides extending between said lateral sides of said absorbent core, an adhesive layer attached to said backsheet and a release paper strip covering the adhesive layer. The longitudinal sides or edges of the pad define side flaps outwardly relative to the longitudinal sides of the absorbent core, and at least two spaced apart elastic members are secured along each longitudinal side flap, with each elastic member having two active ends, at least one of which is located outwardly relative to the corresponding end of the adhesive layer.

65 Claims, 8 Drawing Sheets

SANITARY ELASTICIZED MALE GUARD

FIELD OF THE INVENTION

The present invention relates to sanitary absorbent articles such as absorbent pads designed to eliminate or minimize fluid leakage when worn by incontinent persons. It is particularly related to disposable absorbent pads having elasticized side flaps which reduce fluid side leakage due to insult fluid escaping off the side edges of the pad which is caused by one or more fluid surges or uncontrolled urination by a wearer of the pad.

BACKGROUND OF THE INVENTION

Absorbent pads have been used commercially to improve fluid containment during fluid surge or large quantity of urine discharge experienced by incontinent persons. The term "absorbent pad" as used herein is intended to include male guards, sanitary napkins and the like articles, and is particularly intended to cover male guards having elasticized side flaps containing uniquely placed elastic members with a view toward preventing or minimizing fluid leakage off the pad.

Effective fluid containment in absorbent pads such as, for example, male guards, have been a persistent problem for incontinent persons. In particular, fluid side leakage have been extremely difficult to prevent or minimize when such pads are used by incontinent persons. Typically, these pads are defined by longitudinal and transverse axis, and comprise opposite longitudinal end edges and opposite lateral or side edges between the longitudinal end edges, a backsheet, a liquid permeable topsheet layer disposed on the backsheet, and an absorbent assembly, (core or layer) sandwiched between the backsheet layer and the topsheet. In order to prevent or minimize fluid leakage from the pad several approaches have been suggested in a variety of prior art patents. Some have employed thick absorbent layers for longer fluid retention. Others have incorporated so-called super-absorbent polymers (SAP) in the absorbent layer designed to absorb and retain fluid therein for a sufficient time until the absorbent pad is removed, disposed of and replaced with a fresh pad. Still others have proposed providing the pad with side flaps, including elasticized side flaps in order to control or eliminate side leakage which has been a particularly difficult problem to control in most pads. One early patent which addressed fluid side leakage in absorbent pads is U.S. Pat. No. 4,701,177 issued Oct. 20, 1987 to Ellis et al. This patent discloses curved elongated absorbent pad shaped as an hourglass having a narrower middle portion which is thicker than the end portions of the pad. In a preferred structure, the pad has a backing sheet which extends beyond the absorbent pad and has side edges forming flaps in the narrow region, the flaps being elasticized to gather the flaps and raising them to form a wall on each side of the narrow region of the absorbent pad.

U.S. Pat. No. 5,391,162 issued Feb. 21, 1995 to Widlund et al. describes incontinence guards which comprise an elongated absorbent pad and flexible side flaps disposed at the long side edges of the pad. The flexible side flaps are foldable around the edges of the pad when the article is worn.

U.S. Pat. No. 5,810,800 issued Sep. 22, 1998 describes an incontinence device comprising a liquid pervious topsheet, a liquid impervious backsheet, an absorbent core therebetween and a pair of longitudinally extending elasticized cuffs disposed on the body surface of the topsheet.

U.S. Pat. No. 6,171,290 B1 issued Jan. 9, 2001 to Boisse et al. describes incontinence guards and contains a brief discussion of efforts made by others to improve fluid containment in diapers, guards and sanitary napkins. This patent describes an absorbent article comprising a liquid permeable cover sheet, a liquid repellent barrier sheet, an absorbent layer disposed between said cover sheet and barrier sheet, a pair of side flanges and a pair of elastically extensible element each operatively connected to a side flange.

In a recent patent, i.e., U.S. Pat. No. 6,315,765 B1 issued Nov. 13, 2001 to Datta et al. the patentees describe an elasticized absorbent pad, which includes "guards", used for urinary incontinence. According to this patent, the performance of the pads is enhanced by providing the pads with more effective elasticized side flaps. Several embodiments are described which basically include elasticized side flaps adapted to impart a "bucket shape" to the pad during its use.

Other incontinence guards are disclosed in U.S. Pat. No. 6,328,724 issued to Fransson et al. on Dec. 11, 2001 and U.S. Pat. No. 6,371,950 B1 issued Apr. 16, 2002 to Roslansky et al.

The aforementioned patents which are by no means exhaustive, represent the efforts by developers for providing incontinence guards which are free from fluid leakage, especially side leakage from the article. Notwithstanding these efforts, there is till a dire need for leak-proof male guards for use by incontinent persons, without sacrificing comfort to the wearer.

Accordingly, it is an object of this invention to provide an absorbent pad which, due to its unique construction and configuration, exhibits improved fluid containment capability when used by incontinent persons.

It is also an object of this invention to provide such an absorbent pad which is designed to prevent or minimize side leakage of fluid from the pad due to fluid surge or fluid insult experienced by an incontinent person wearing the pad.

It is a further object of this invention to provide an absorbent pad, in particular male guards, having the foregoing features without sacrificing comfort to the wearer.

The foregoing and other features and improved attributes of the absorbent pads of the present invention will be comprehended from the ensuing detailed description and the accompanying drawings. Throughout the present application the term "absorbent pad" as used herein is intended to include sanitary napkins and the like articles, especially male guards.

SUMMARY OF THE INVENTION

In order to achieve the foregoing objects and advantageous features, the present invention provides a pad which is especially useful as a male guard comprising:
1. nonwoven coversheet (bodyside liner)
2. acquisition/distribution layer
3. absorbent core
4. crotch elastic elements
5. backsheet (garment side liner)
6. adhesive liner attached to backsheet
7. a strip of paper such as silicone paper releaseably attached to the under surface of the adhesive strip The general construction and the relationship among the various layers which form the male guard of the present invention are as follows: A liquid permeable nonwoven coversheet which normally faces and is in contact with the skin of the wearer of the article, and backsheet film which is liquid (fluid) impermeable but vapor permeable defines the garment side away from the skin of wearer. An absorbent assembly, core of layer is disposed between the coversheet and the backsheet and an acquisition/distribution layer is between the coversheet and the absorbent core layer. The underside of the backsheet, i.e., its garment side surface is covered with an adhesive strip which is somewhat coextensive with the length of the backsheet. A strip of release paper such as silicone paper covers the garment side surface of the adhesive layer and has two longitudinal ends.

The pad itself is defined by two opposed lateral sides and two opposed longitudinal sides which extend between the pad's lateral sides. At least two crotch elastic elements are disposed on each longitudinal side of the pad, one of these elastic elements is an inner elastic element and is about ¼ inch from the longitudinal side edge of the core layer, or as close thereto as possible and the other elastic element is an outer elastic element and is spaced apart therefrom, about 0 to about 1 inch. The elastic members gather the side flaps of the pad toward the middle of the pad and provide an effective seal against fluid leakage caused by large or sudden insult of fluid during periods of incontinence.

BRIEF DESCRIPTION OF THE DRAWINGS

In the drawings, wherein like reference numerals are employed to designate like parts or elements.

DETAILED DESCRIPTION OF THE INVENTION

Figure 1:
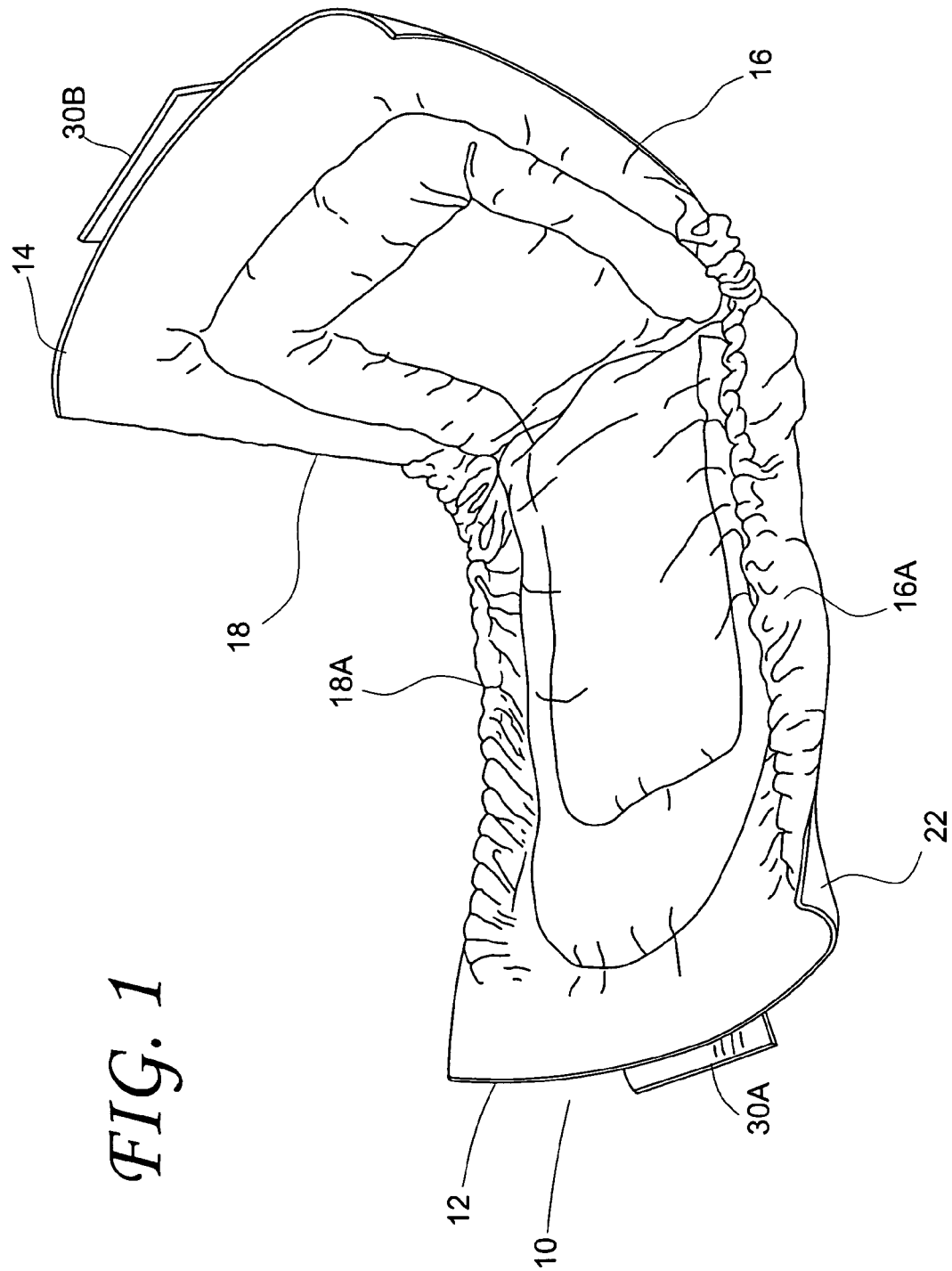
FIG. 1 is a perspective view of a male guard according to one embodiment of the present invention.

Referring to FIGS. 1–4A of the drawings, there is shown in FIG. 1, a male guard formed according to one embodiment of the present invention. The male guard illustrated therein may be used by incontinent persons, particularly men, for absorption of body fluids or excrements during a period of incontinence. The male guard of the present invention generally comprises the following component parts:

1. nonwoven coversheet (bodyside liner)
2. acquisition/distribution layer
3. absorbent core (layer)
4. crotch elastic elements
5. backsheet (composite film/nonwoven layer)
6. adhesive layer attached to the backsheet
7. release paper attached to the adhesive layer Referring to FIG. 1, the male guard of the present invention designated by 10 is defined by opposite lateral end edges 12 and 14 and longitudinal side edges 16 and 18 which extend between the end edges 12 and 14. The arrowed lines A—A and B—B (see FIG. 2) represent the longitudinal axis and the transverse (lateral) axis, respectively, of the male guard 10. Typically such male guards are from about 13 to about 25 inches long and from about 10 to about 16 inches wide. In other words, the longitudinal sides edges of these guards are from about 13 to about 25 inches long and their lateral side edges are from about 10 to about 16 inches wide when both are measured in fully stretched position as shown in FIG. 2.

Figure 2:
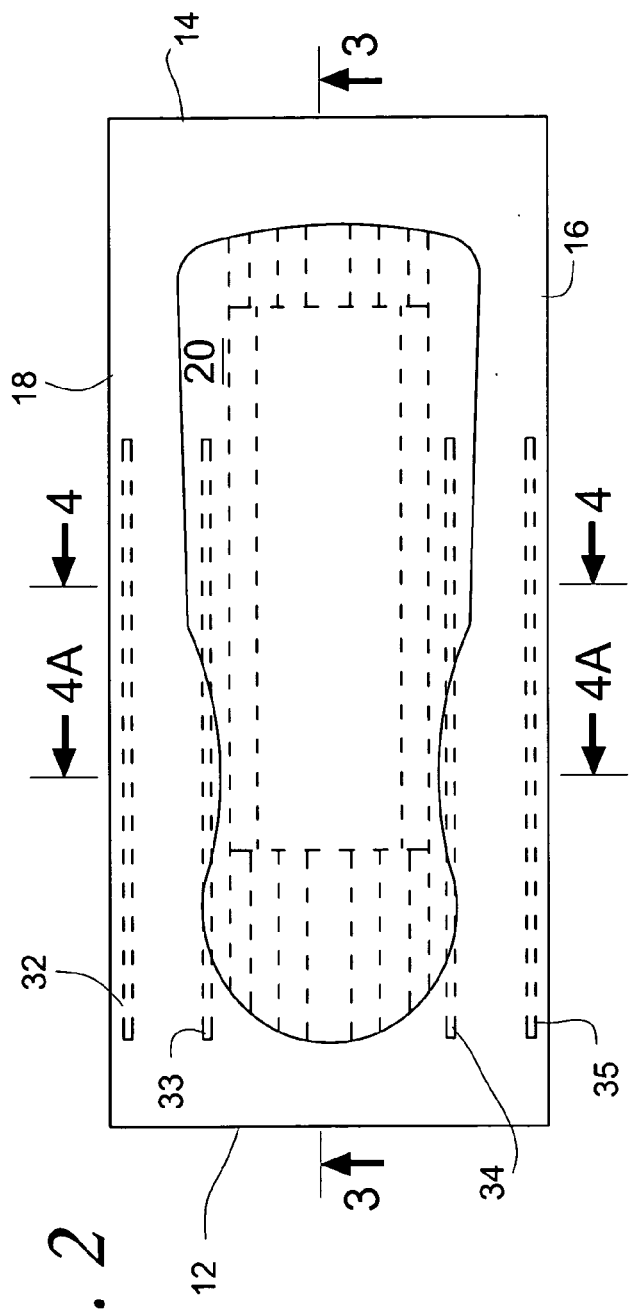
FIG. 2 is stretched top view of the male guard shown in FIG. 1.
Figure 3:
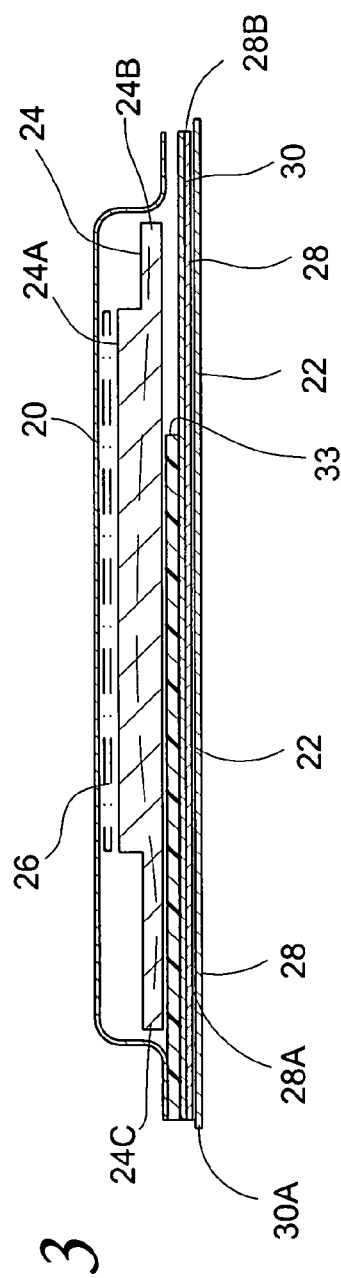
FIG. 3 is a sectional view taken along the line 3—3 of FIG. 2.
Figure 2A:
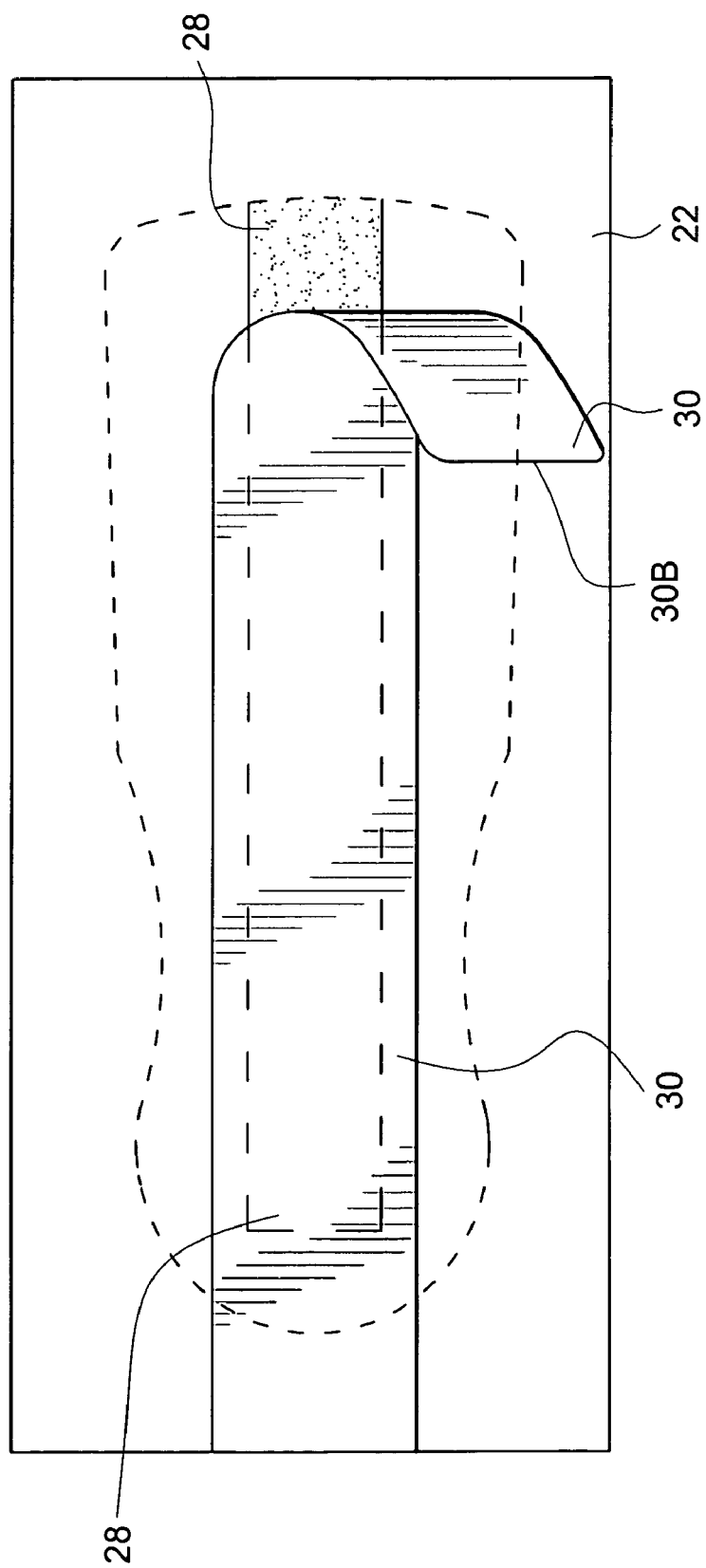
FIG. 2A is a stretched bottom view of the male guard shown in FIG. 1.
Figure 4:
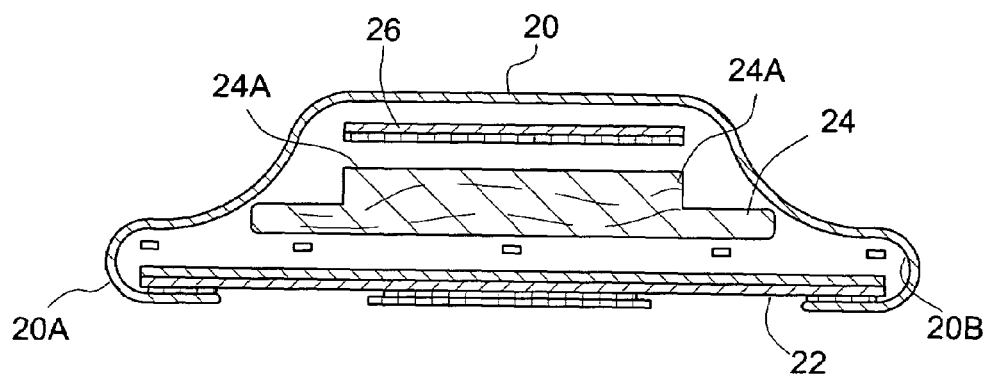
FIG. 4 is a sectional view taken along the line 4—4 of FIG. 2.
Figure 4A:
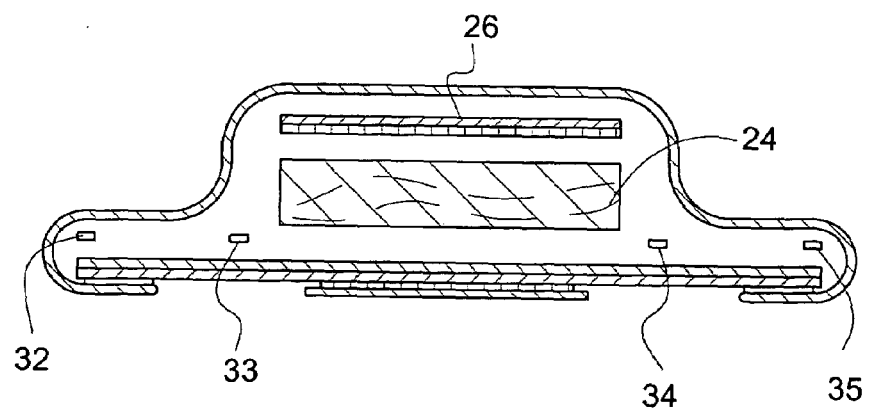
FIG. 4A is a sectional view taken along the line 4A—4A in the crotch area of the absorbent pad of FIG. 2.

As is more clearly shown in FIGS. 2, 3 and 4, the male guard 10 comprises liquid (fluid) permeable topsheet 20, a liquid (fluid) impermeable backsheet 22, and an absorbent core or layer 24 disposed between the topsheet 20 and backsheet 22. The absorbent core 24 has a raised ridge 24A between the longitudinal ends 24B and 24C of the absorbent core 24 and thus defines a shaped absorbent core. It can be seen from FIGS. 1–4, that the topsheet 20 is normally in contact with the skin of the wearer of the guard and therefore it is also referred to as the bodyside liner, and the backsheet 22 is on the opposite side, i.e., the side away from the skin of the wearer or the garment side, and therefore it is sometimes referred to as the backing liner or garment side liner. The male guard shown in FIGS. 1–4 can also be provided with an acquisition layer 26 disposed between the top surface of the raised ridge 24A of the absorbent core 24 and the topsheet (coversheet) 20. In addition, an adhesive layer 28 having ends 28A, 28B is attached to the underside (garment side) of the backsheet 22, and a strip of paper such as silicone paper 30 is releasably secured to the adhesive layer 28 and includes a back end 30A and front end 30B. Before use, either end of the silicone release paper may be gripped and the paper detached from the adhesive layer.

The coversheet 20 is a liquid and vapor permeable nonwoven such as described in U.S. Pat. No. 6,306,121, issued Oct. 23, 2001 to the assignee of this application, the disclosure of which is fully incorporated herein by reference. Thus, the coversheet may be made of a liquid pervious, soft compliant material which is non-irritating and is skin friendly. By way of examples, such materials include porous foams, reticulated foams, plastics, natural fibers such as woods or cotton fibers, synthetic fibers made of polyester or poly-propylene available from First Quality Fibers, Inc., McElhattan, Pa., or made from a suitable combination of said liquids.

The acquisition/distribution layer 26 serves the usual function of distributing the fluid or liquid which passes through the coversheet. The acquisition layer is usually made of chemically bonded nonwoven polypropylene available from American Nonwoven, Columbus, Mo. Preferably, this layer is coextensive with the width of the absorbent core or layer 24. The acquisition layer 26 may be a single layer having a basis weight of about 50 or less grams per square meter (GSM). Alternatively, the acquisition layer may be a composite which consists of two layers, an acquisition layer on top of a layer of air laid material. The air laid material may be made of a mixture of wood pulp fibers (fluff) and superabsorbent polymer (SAP) in which the amount of SAP is less than about 28 weight percent of the mixture. Suitable superabsorbent polymers include polyacrylamide, polyvinyl alcohol, polyvinyl ether, ethylene-maleic anhydride copolymers, polyacrylates, polyacrylamides, polyvinylpyrrolidone, polyacrylates, isobutylene-maleic anhydride copolymers, or mixtures of said polymers and copolymers. Crosslinked polyacrylic acid is particularly effective absorbent when mixed with fiberized wood (fluff) in an amount between about 3 to about 80 weight percent based on the weight of the fluff-SAP mixture. When a composite is used in the acquisition layer, the dry laid layer and the acquisition layer may be attached together by the heat or a suitable adhesive, or the two layers may simply be maintained in contact with one another.

The core layer 24 is also made of a mixture of fluff and SAP in which the SAP constitutes less than about 28 weight percent of the mixture. The SAP particles used in the mixture which forms the core layer 24 are usually in the form of agglomerates or globs rather than discrete particulate matters. The absorbent core 24 may be formed from a wide variety of liquid absorbent materials of the type used in making absorbent disposable diapers and other absorbent articles. This core may be made of wood pulp fibers and superabsorbent polymers (SAP) such as IM 7000 series available from Clarian Products, Inc., Portsmouth, Va. and Chemdal 2000 series available from Chemdal, Inc., Palantine, Ill. Alternatively, the absorbent core may be made of dual construction, in which case, the SAP may be placed between each layer of the absorbent material.

The composite backing (backsheet) 22 is usually a composite of a polyethylene layer laminated to a layer of nonwoven, and is liquid, air and vapor impermeable, is placed under the absorbent core 24 to prevent body exudates from leaking and otherwise soiling the user's bed and clothing. The width and length of the backsheet 22 are generally at least equal to the width and length of the absorbent core 24. Polyethylenes suitable as a composite backing sheet for the purpose of this invention are available from Clopay Plastics, Cincinnati, Ohio. This is approximately 0.7 mil polyethylene film laminated onto 17 GSM spunbonded nonwoven. It is preferable to use a composite as hereinabove described but wherein the film is vapor permeable.

An adhesive strip 28 is attached to the bottom surface of the backsheet 22. The adhesive strip does not span the full length of the pad so that, as will be hereinafter described in more detail, one active end of the crotch elastic (as hereinafter described) is disposed outwardly relative to the end of the adhesive strip while the other end of the crotch elastic is disposed inwardly relative to the end of the adhesive strip, as shown in FIG. 3. A release paper such as, e.g., silicone coated paper strip 30 is releasably attached to the adhesive strip 28 and is coterminous with the backsheet 22. Thus, the ends 30A, 30B of the silicone paper strip 30 extend beyond the ends of the adhesive strip 28.

A principal feature of the male guard of the present invention is the provision and location of elastic elements in the longitudinal sides, i.e., the side flaps of the male guard. In one embodiment the guard is provided with five elastic elements 32, 33, 34, 35 and 36 as shown in FIG. 2. Two crotch elastic elements 32 and 33 are disposed along one longitudinal side of the absorbent pad, one of which, i.e., the outer elastic element 32 is located near the side flap or edge 18 and the other, i.e., inner elastic element 33 is located adjacent the longitudinal edge secured below the absorbent core 24. Disposed on the opposite longitudinal side of the absorbent core 24 are the elastic elements 34 and 35 with inner elastic element 34 located adjacent the longitudinal edge below the absorbent core 24 and the other elastic elements, i.e., elastic element 35 is located near the longitudinal side edge 16 of the pad. Elastic elements 32 and 33 cause the side edge or side flap 18 to gather about the middle to form a gathered portion 18A. Similarly, the elastic elements 34 and 35 cause the side edge or side flaps 16 to gather about the middle to form the gathered portion 16A. In the embodiment shown in FIGS. 1–3, each of the elastic elements has two active ends; one active end which terminates exteriorly relative to the end 28A of the adhesive layer 28 and an opposite end which terminates interiorly relative to the other end 28B of the adhesive strip. By locating the elastic elements 33 and 34 adjacent to or as close to the longitudinal edges of the absorbent core layer 24, there is little or no likelihood for these elastic elements to be outside the plane of the pad while insuring against fluid leakage, and to exert forces on the core 24 so as to gather the side flaps and the core thus resulting in a pad having a cup shaped configuration.

In the embodiment illustrated in FIG. 2 each of the elastic elements 32–35 are secured (attached or glued) at the longitudinal edges of the absorbent pad between the composite backsheet 22 and the coversheet 20. Furthermore, the coversheet sides fold over the composite backsheet as shown by 20A and 20B in FIG. 4A. Each of these elastic elements extend from the back end of the absorbent core 24 and terminates inwardly relative to the front end of the core. The elastic elements 32–35 are usually coterminous with each other at both ends and serve to form the gather portions 16A and 18A (see FIG. 1). The elastic elements are secured under tension of from about 40 to about 200 percent. In a preferred construction, the outer elastics 32 and 35 are somewhat wider than the inner elastics 33 and 34 or have a larger cross sectional area. This improves gathering of the side flaps and thus results in improved leakage protection.

Figure 5:
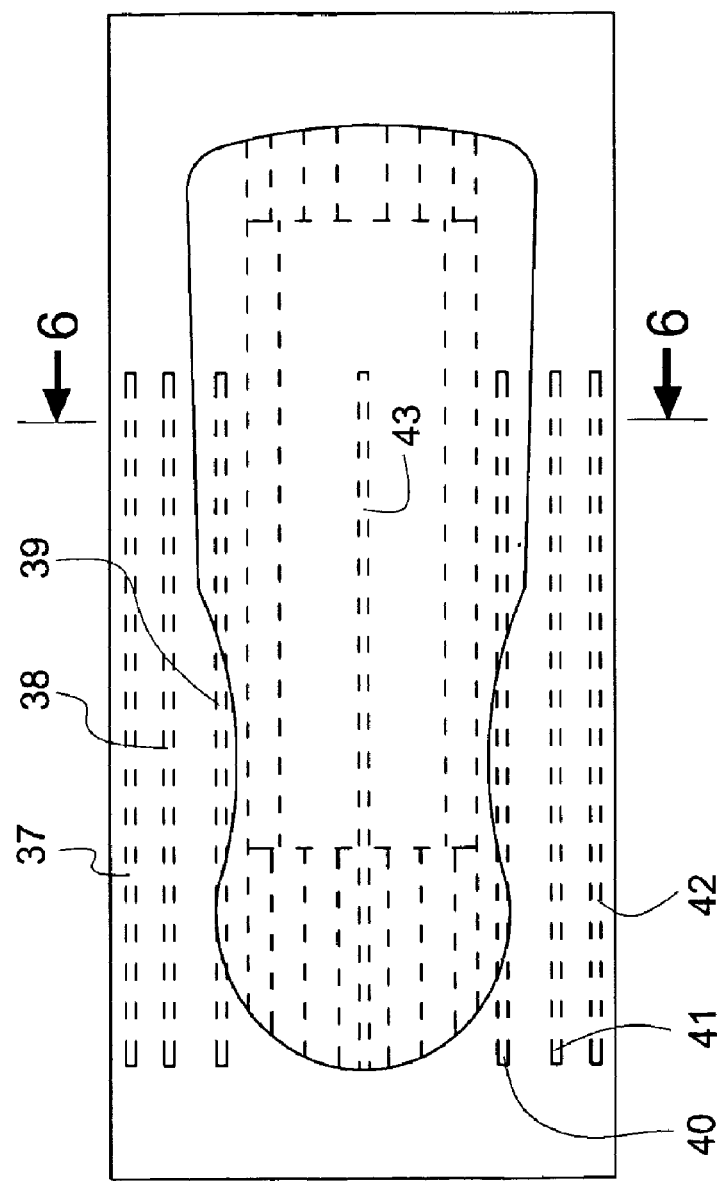
FIG. 5 is a stretched top view similar to FIG. 2 but illustrating another embodiment of this invention using three elastics on each side flap.

FIG. 5 illustrates another embodiment of the male guard of the present invention which is similar in construction to the embodiment shown in FIG. 2, but wherein the male guard is provided with seven (7) elastic elements, one middle elastic element and three spaced apart elastic elements on each side of the middle elastic element. Thus, the male guard 10 in this embodiment has side elastic elements 37, 38, 39, 40, 41 and 42, and a middle elastic 43 all secured between the coversheet and the backsheet as in the embodiment shown in FIG. 2. The middle elastic 43 is secured between the absorbent core and the backsheet.

Figure 5A:
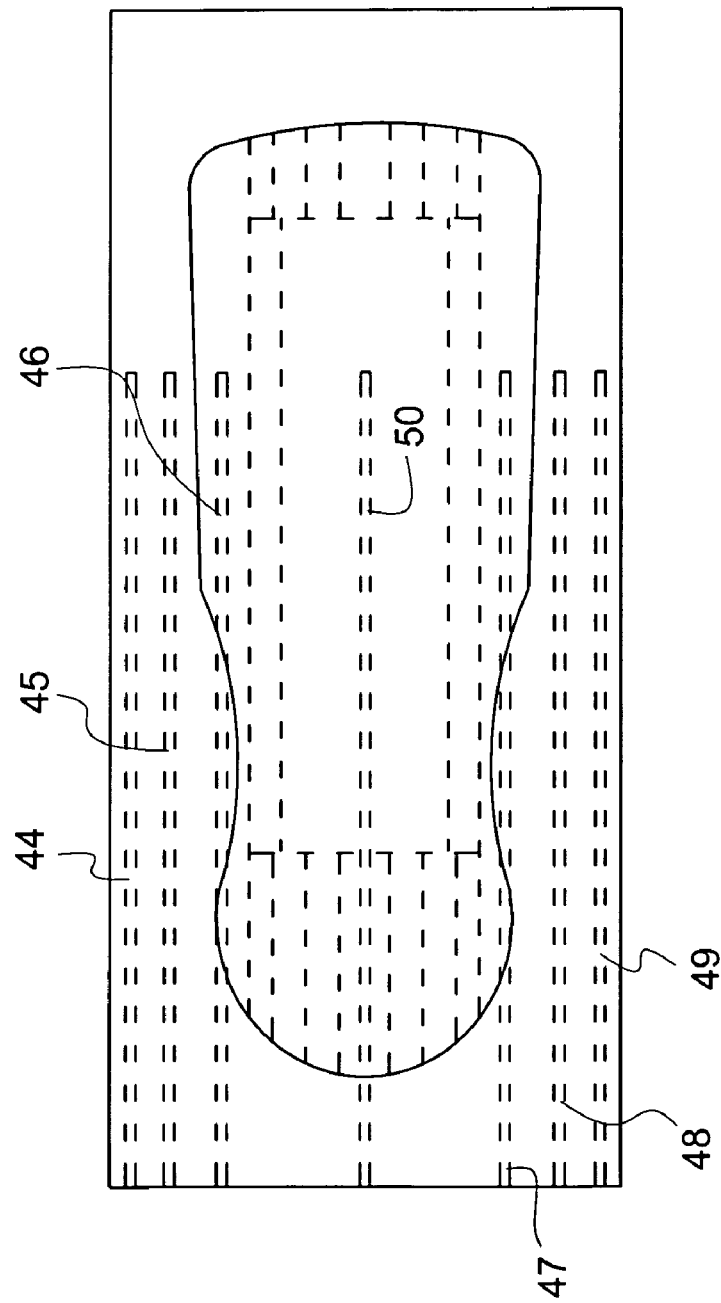
FIG. 5A is a stretched top view similar to FIG. 5 according to a further embodiment of this invention wherein the elastic elements extend to the male guard's back end.

FIG. 5A illustrates a further embodiment of the male guard of the present invention similar to FIG. 5 but wherein the back ends of the side elastic elements 44, 45, 46, 47, 48 and 49 and the back end of the middle elastic element 50 all terminate at the product ends.

Figure 5B:
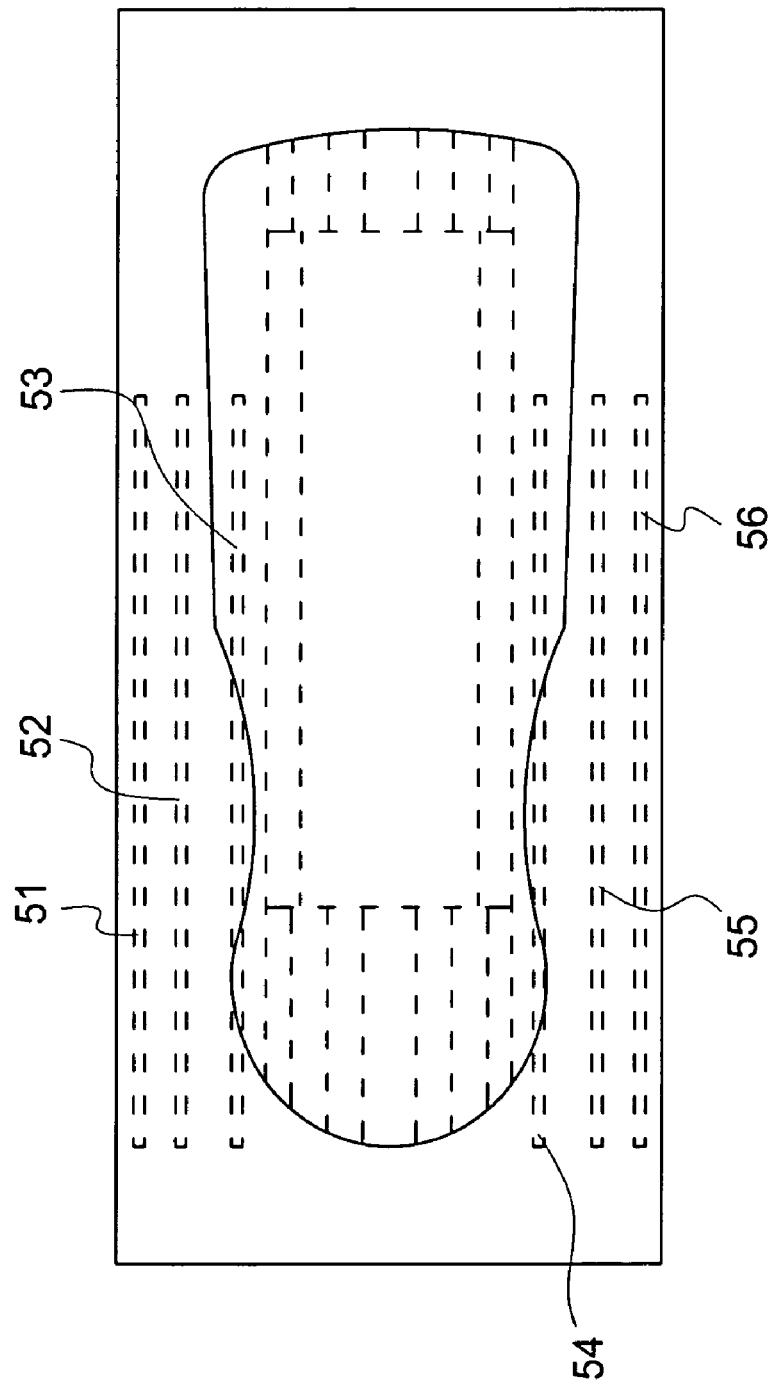
FIG. 5B is a stretched top view similar to FIG. 5 according to still another embodiment of the present invention wherein no middle elastic member is employed.
Figure 6:
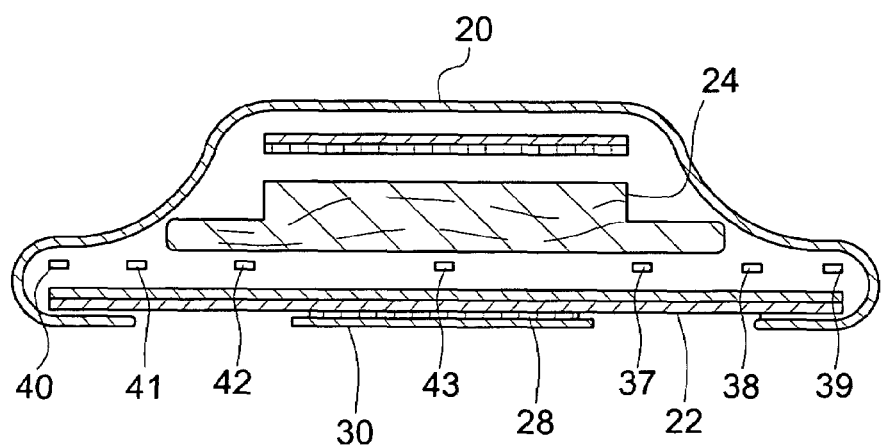
FIG. 6 is a sectional view taken along the line 6—6 of FIG. 5.

FIG. 5B illustrates a still different embodiment of the male guard which is similar to FIG. 5A except that no middle elastic is used. Thus, only side elastics 51, 52, 53, 54, 55 and 56 are provided, secured between the backsheet and the coversheet as in the previous embodiments.

The locations and relative spacings of the elastic elements in the male guard of the present invention as hereinbefore described affords protection against fluid leaks from the male guard, particularly during periods of incontinence. Fluid leakage may be further prevented or reduced by providing an absorbent core which itself is capable of controlling the fluid surge initially so that fluid leakage can be more easily controlled and prevented by incorporation of elastic elements in the manner described herein. This may be accomplished by providing, in the absorbent layer, one or more zones (areas) which are enriched in fluff-SAP content relative to the remaining areas of the absorbent layer. These fluff-SAP enriched zones contain a fluff-SAP mixture which is from about 1.5 to about 5.0, preferably from about 2.0 to about 3.0 times the amount of fluff-SAP mixture in the non-enriched zones, as more fully described in copending application Ser. No. 10/066,731 filed Feb. 4, 2002, the disclosure of which is fully incorporated herein by reference.

The foregoing description of the different embodiments of the present invention suggest several changes and modifications to one skilled in the art. Such changes and modifications are nevertheless within the scope of this invention.

The invention claimed is:

1. A disposable sanitary absorbent pad defined by opposed lateral sides and opposed longitudinal sides extending between said lateral sides, said sanitary absorbent pad comprising a first longitudinal end portion and a second longitudinal end portion, said absorbent pad comprising:
   a liquid permeable topsheet,
   a backsheet,
   an absorbent core layer disposed between said topsheet and said backsheet, said absorbent core layer having opposed lateral side edges and opposed longitudinal side edges extending between said lateral edges,
   an adhesive layer attached to said backsheet, said adhesive layer having a first longitudinal end at said first longitudinal end portion of said sanitary absorbent pad and a second longitudinal end at said second longitudinal end portion of said sanitary absorbent pad,
   a release paper strip covering said adhesive layer, said release paper strip having two longitudinal ends, at least one of which extends beyond the longitudinal end of said adhesive strip,
   side flaps disposed laterally outward of said longitudinal sides of said absorbent core layer,
   at least two spaced apart elastic members secured along each longitudinal side flap of said absorbent pad between said lateral side edges of said absorbent pad, an inner elastic member disposed below said absorbent core layer and spaced less than ¼ inch from the longitudinal side edge of said absorbent core layer and an outer elastic member spaced from about 0 to about 1 inch from said longitudinal side edge, each of said elastic members having two active ends, one of said active ends being located longitudinally outward relative to said first longitudinal end of said adhesive layer and said other of said active ends being located longitudinally inward relative to said second longitudinal end of said adhesive layer.

2. A sanitary absorbent pad as in claim 1 further including another elastic member extending between the longitudinal sides of said absorbent core wherein said another elastic member has two active ends, one of said active ends being secured to one lateral edge of said absorbent pad.

3. A disposable sanitary absorbent pad as in claim 1 wherein one of said elastic members has a larger cross section than the other elastic members.

4. A disposable sanitary absorbent pad as in claim 2 wherein one of said elastic members has a larger cross section than the other elastic members.

5. A disposable sanitary absorbent pad as in claim 1 wherein said backsheet is fluid impermeable but vapor permeable.

6. A disposable sanitary absorbent pad as in claim 2 wherein said backsheet is fluid impermeable but vapor permeable.

7. A disposable sanitary absorbent pad as in claim 3 wherein said backsheet is fluid impermeable but vapor permeable.

8. A disposable sanitary absorbent pad as in claim 4 wherein said backsheet is fluid impermeable but vapor permeable.

9. A disposable absorbent article as in claim 1 wherein said absorbent core is made of a mixture of fluff and superabsorbent polymer wherein said superabsorbent polymer constitutes less than about 27 weight percent of said mixture.

10. A disposable absorbent article as in claim 2 wherein said absorbent core is made of a mixture of fluff and superabsorbent polymer wherein said superabsorbent polymer constitutes less than about 27 weight percent of said mixture.

11. A disposable absorbent article as in claim 3 wherein said absorbent core is made of a mixture of fluff and superabsorbent polymer wherein said superabsorbent polymer constitutes less than 27 weight percent of said mixture.

12. A disposable absorbent article as in claim 4 wherein said absorbent core is made of a mixture of fluff and superabsorbent polymer wherein said superabsorbent polymer constitutes less than 27 weight percent of said mixture.

13. A disposable absorbent article as in claim 5 wherein said absorbent core is made of a mixture of fluff and superabsorbent polymer wherein said superabsorbent polymer constitutes less than about 27 weight percent of said mixture.

14. A disposable absorbent article as in claim 6 wherein said absorbent core is made of a mixture of fluff and superabsorbent polymer wherein said superabsorbent polymer constitutes less than about 27 weight percent of said mixture.

15. A disposable absorbent article as in claim 7 wherein said absorbent core is made of a mixture of fluff and superabsorbent polymer wherein said superabsorbent polymer constitutes less than about 27 weight percent of said mixture.

16. A disposable absorbent article as in claim 8 wherein said absorbent core is made of a mixture of fluff and superabsorbent polymer wherein said superabsorbent polymer constitutes less than about 27 weight percent of said mixture.

17. A disposable absorbent article as in claim 1 further comprising an acquisition layer disposed between said topsheet and said absorbent core.

18. A disposable absorbent article as in claim 2 further comprising an acquisition layer disposed between said topsheet and said absorbent core.

19. A disposable absorbent article as in claim 3 further comprising an acquisition layer disposed between said topsheet and said absorbent core.

20. A disposable absorbent article as in claim 4 further comprising an acquisition layer disposed between said topsheet and said absorbent core.

21. A disposable absorbent article as in claim 5 further comprising an acquisition layer disposed between said topsheet and said absorbent core.

22. A disposable absorbent article as in claim 6 further comprising an acquisition layer disposed between said topsheet and said absorbent core.

23. A disposable absorbent article as in claim 7 further comprising an acquisition layer disposed between said topsheet and said absorbent core.

24. A disposable absorbent article as in claim 8 further comprising an acquisition layer disposed between said topsheet and said absorbent core.

25. A disposable absorbent article as in claim 9 further comprising an acquisition layer disposed between said topsheet and said absorbent core.

26. A disposable absorbent article as in claim 10 further comprising an acquisition layer disposed between said topsheet and said absorbent core.

27. A disposable absorbent article as in claim 11 further comprising an acquisition layer disposed between said topsheet and said absorbent core.

28. A disposable absorbent article as in claim 12 further comprising an acquisition layer disposed between said topsheet and said absorbent core.

29. A disposable absorbent article as in claim 13 further comprising an acquisition layer disposed between said topsheet and said absorbent core.

30. A disposable absorbent article as in claim 14 further comprising an acquisition layer disposed between said topsheet and said absorbent core.

31. A disposable absorbent article as in claim 15 further comprising an acquisition layer disposed between said topsheet and said absorbent core.

32. A disposable absorbent article as in claim 16 further comprising an acquisition layer disposed between said topsheet and said absorbent core.

33. A disposable absorbent article as in claim 17 wherein said acquisition layer comprises an air laid layer.

34. A disposable absorbent article as in claim 18 wherein said acquisition layer comprises an air laid layer.

35. A disposable absorbent article as in claim 19 wherein said acquisition layer comprises an air laid layer.

36. A disposable absorbent article as in claim 20 wherein said acquisition layer comprises an air laid layer.

37. A disposable absorbent article as in claim 21 wherein said acquisition layer comprises an air laid layer.

38. A disposable absorbent article as in claim 22 wherein said acquisition layer comprises an air laid layer.

39. A disposable absorbent article as in claim 23 wherein said acquisition layer comprises an air laid layer.

40. A disposable absorbent article as in claim 24 wherein said acquisition layer comprises an air laid layer.

41. A disposable absorbent article as in claim 25 wherein said acquisition layer comprises an air laid layer.

42. A disposable absorbent article as in claim 26 wherein said acquisition layer comprises an air laid layer.

43. A disposable absorbent article as in claim 27 wherein said acquisition layer comprises an air laid layer.

44. A disposable absorbent article as in claim 28 wherein said acquisition layer comprises an air laid layer.

45. A disposable absorbent article as in claim 29 wherein said acquisition layer comprises an air laid layer.

46. A disposable absorbent article as in claim 30 wherein said acquisition layer comprises an air laid layer.

47. A disposable absorbent article as in claim 31 wherein said acquisition layer comprises an air laid layer.

48. A disposable absorbent article as in claim 32 wherein said acquisition layer comprises an air laid layer.

49. A disposable absorbent article as in claim 33 wherein said air laid layer is made of a mixture of fluff and superabsorbent polymer, wherein said superabsorbent polymer constitutes less than about 27 weight percent of said mixture.

50. A disposable absorbent article as in claim 34 wherein said air laid layer is made of a mixture of fluff and superabsorbent polymer, wherein said superabsorbent polymer constitutes less than about 27 weight percent of said mixture.

51. A disposable absorbent article as in claim 35 wherein said air laid layer is made of a mixture of fluff and superabsorbent polymer, wherein said superabsorbent polymer constitutes less than about 27 weight percent of said mixture.

52. A disposable absorbent article as in claim 36 wherein said air laid layer is made of a mixture of fluff and superabsorbent polymer, wherein said superabsorbent polymer constitutes less than about 27 weight percent of said mixture.

53. A disposable absorbent article as in claim 37 wherein said air laid layer is made of a mixture of fluff and superabsorbent polymer, wherein said superabsorbent polymer constitutes less than about 27 weight percent of said mixture.

54. A disposable absorbent article as in claim 38 wherein said air laid layer is made of a mixture of fluff and superabsorbent polymer, wherein said superabsorbent polymer constitutes less than about 27 weight percent of said mixture.

55. A disposable absorbent article as in claim 39 wherein said air laid layer is made of a mixture of fluff and superabsorbent polymer, wherein said superabsorbent polymer constitutes less than about 27 weight percent of said mixture.

56. A disposable absorbent article as in claim 40 wherein said air laid layer is made of a mixture of fluff and superabsorbent polymer, wherein said superabsorbent polymer constitutes less than about 27 weight percent of said mixture.

57. A disposable absorbent article as in claim 41 wherein said air laid layer is made of a mixture of fluff and superabsorbent polymer, wherein said superabsorbent polymer constitutes less than about 27 weight percent of said mixture.

58. A disposable absorbent article as in claim 42 wherein said air laid layer is made of a mixture of fluff and superabsorbent polymer, wherein said superabsorbent polymer constitutes less than about 27 weight percent of said mixture.

59. A disposable absorbent article as in claim 43 wherein said air laid layer is made of a mixture of fluff and superabsorbent polymer, wherein said superabsorbent polymer constitutes less than about 27 weight percent of said mixture.

60. A disposable absorbent article as in claim 44 wherein said air laid layer is made of a mixture of fluff and superabsorbent polymer, wherein said superabsorbent polymer constitutes less than about 27 weight percent of said mixture.

61. A disposable absorbent article as in claim 45 wherein said air laid layer is made of a mixture of fluff and superabsorbent polymer, wherein said superabsorbent polymer constitutes less than about 27 weight percent of said mixture.

62. A disposable absorbent article as in claim 46 wherein said air laid layer is made of a mixture of fluff and superabsorbent polymer, wherein said superabsorbent polymer constitutes less than about 27 weight percent of said mixture.

63. A disposable absorbent article as in claim 47 wherein said air laid layer is made of a mixture of fluff and superabsorbent polymer, wherein said superabsorbent polymer constitutes less than about 27 weight percent of said mixture.

64. A disposable absorbent article as in claim 48 wherein said air laid layer is made of a mixture of fluff and superabsorbent polymer, wherein said superabsorbent polymer constitutes less than about 27 weight percent of said mixture.

65. A disposable absorbent article as in claims 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, or 64, wherein said core comprises at least one area having higher gram basis weight than the remaining areas of said core.

* * * * *